(12) United States Patent
Sakura

(10) Patent No.: US 7,850,700 B2
(45) Date of Patent: Dec. 14, 2010

(54) TISSUE LIFTING DEVICE AND METHOD

(76) Inventor: Chester Y. Sakura, 12900 Sandia Point N.E., Albuquerque, NM (US) 87111

( * ) Notice: Subject to any disclaimer, the term of this patent is extended or adjusted under 35 U.S.C. 154(b) by 1097 days.

(21) Appl. No.: 10/848,698

(22) Filed: May 19, 2004

(65) Prior Publication Data

US 2005/0261737 A1 Nov. 24, 2005

(51) Int. Cl.
  *A61B 17/04* (2006.01)
  *A61B 17/12* (2006.01)
  *A61L 17/00* (2006.01)
(52) U.S. Cl. .................................. 606/144; 606/228
(58) Field of Classification Search ......... 606/139–141, 606/144, 151, 213, 216, 220, 221, 233, 228; 600/201, 213, 215, 217
  See application file for complete search history.

(56) References Cited

U.S. PATENT DOCUMENTS

| | | | | |
|---|---|---|---|---|
| 4,570,306 A | * | 2/1986 | Eyler | 24/114.3 |
| 4,790,849 A | | 12/1988 | Terino | |
| 4,799,495 A | * | 1/1989 | Hawkins et al. | 600/567 |
| 4,932,962 A | * | 6/1990 | Yoon et al. | 606/224 |
| 4,969,901 A | | 11/1990 | Binder | |
| 5,127,916 A | * | 7/1992 | Spencer et al. | 606/185 |
| 5,217,494 A | | 6/1993 | Coggins | |
| 5,370,661 A | * | 12/1994 | Branch | 606/232 |
| 5,413,600 A | | 5/1995 | Mittelman | |
| 5,500,000 A | * | 3/1996 | Feagin et al. | 606/232 |
| 5,607,477 A | | 3/1997 | Schindler | |
| 5,662,714 A | | 9/1997 | Charvin | |
| 5,695,525 A | | 12/1997 | Mulhauser | |
| 5,723,009 A | | 3/1998 | Frechet | |
| 5,746,762 A | | 5/1998 | Bass | |
| 5,782,913 A | | 7/1998 | Schindler | |
| 5,931,855 A | | 8/1999 | Buncke | |
| 5,941,910 A | | 8/1999 | Schindler | |
| 5,964,782 A | * | 10/1999 | Lafontaine et al. | 606/213 |
| 5,968,097 A | | 10/1999 | Frechet | |
| 6,030,393 A | * | 2/2000 | Corlew | 606/148 |
| 6,110,183 A | * | 8/2000 | Cope | 606/139 |
| 6,241,747 B1 | * | 6/2001 | Ruff | 606/216 |
| 6,277,150 B1 | | 8/2001 | Crawley | |

(Continued)

OTHER PUBLICATIONS

James D. Williams, MD, "Rhytidectomy, SMAS Facelift," eMedicine, Feb. 5, 2004., pp. 1-7, http://www.emedicine.com/ent/topic133.htm.

(Continued)

*Primary Examiner*—(Jackie) Tan-Uyen T Ho
*Assistant Examiner*—Dianne Dornbusch
(74) *Attorney, Agent, or Firm*—Woodard, Emhardt, Moriarty, McNett & Henry LLP

(57) ABSTRACT

A surgical apparatus with an insertion tool and fixation device for lifting or remodeling soft tissue as described. A combination of a fixation device and insertion tool allows for incremental release and engagement of the fixation device, which is supplied with prongs to grasp the soft tissue and hold on the other end to allow suture lifting of the soft tissue. The careful deployment of the fixation device and the manipulation and tension on the insertion tool allows a gradual, adjustable, and uniform lifting of the soft tissue that are to be remodeled.

34 Claims, 8 Drawing Sheets

U.S. PATENT DOCUMENTS

| | | | |
|---|---|---|---|
| D462,766 S | 9/2002 | Jacobs | |
| 6,482,178 B1* | 11/2002 | Andrews et al. | 604/164.01 |
| 6,485,503 B2 | 11/2002 | Jacobs | |
| 7,247,160 B2* | 7/2007 | Seiler et al. | 606/167 |
| 7,326,222 B2* | 2/2008 | Dreyfuss et al. | 606/144 |
| 7,608,092 B1* | 10/2009 | Schaffhausen | 606/232 |
| 7,736,292 B2* | 6/2010 | Hermann et al. | 600/7 |
| 2001/0025190 A1 | 9/2001 | Weber | |
| 2001/0037130 A1* | 11/2001 | Adams | 606/220 |
| 2001/0039423 A1 | 11/2001 | Skiba | |
| 2002/0019670 A1 | 2/2002 | Crawley | |
| 2002/0022861 A1 | 2/2002 | Jacobs | |
| 2002/0026127 A1* | 2/2002 | Balbierz et al. | 600/567 |
| 2002/0120338 A1 | 8/2002 | Boyer | |
| 2002/0173848 A1 | 11/2002 | Sachs | |
| 2002/0198544 A1* | 12/2002 | Uflacker | 606/144 |
| 2003/0023313 A1 | 1/2003 | Byers | |
| 2003/0036770 A1 | 2/2003 | Markman | |
| 2003/0069602 A1 | 4/2003 | Jacobs | |
| 2003/0074021 A1 | 4/2003 | Morriss | |
| 2003/0074023 A1 | 4/2003 | Kaplan | |
| 2003/0212394 A1* | 11/2003 | Pearson et al. | 606/41 |
| 2004/0059328 A1* | 3/2004 | Daniel et al. | 606/41 |
| 2004/0127765 A1* | 7/2004 | Seiler et al. | 600/7 |
| 2006/0276680 A1* | 12/2006 | Seiler et al. | 600/7 |
| 2007/0106108 A1* | 5/2007 | Hermann et al. | 600/7 |
| 2009/0209804 A1* | 8/2009 | Seiler et al. | 600/7 |

OTHER PUBLICATIONS

AAFPRS—"Procedures Understanding Forehead & Brow Lift Surgery," Facial Plastic Surgery, pp. 1-3, http://www.facial-plastic-surgery.org/patient/procedures/forehead_lifts.html.

AAFPRS—"Glossary of Terms," Facial Plastic Surgery, pp. 1-2,: http://www.facial-plastic-surgery.org/patient/procedures/glossary.html.

MayoClinic.com—"Saving face: The nips and tucks of face-lifts," pp. 1-3, http://www.mayoclinic.com/invoke.cfm?id+HQ01326.

Endotine Midface, Multipoint Fixation/Simple Procedure, "Multipoint Fixation Delivers Results in MID Face Suspension," pp. 1-2, http://www.coaptsystems.com/products/mid_face.html.

Endotine Forehead, Control of Fixation/The Design/MultiPoint Fixation, "For Control of Fixation in Open and Endoscopic Brow Procedures," pp. 1-3, http://www.coaptsystems.com/products/products_endotine.html.

Rebecca Bryant, staff correspondent, Facelift Innovation, "Doctor's new 'smart' suture permits progressive facelift," *Cosmetic Surgery Times*, Vancouver, British Columbia, Jun. 2004.

\* cited by examiner

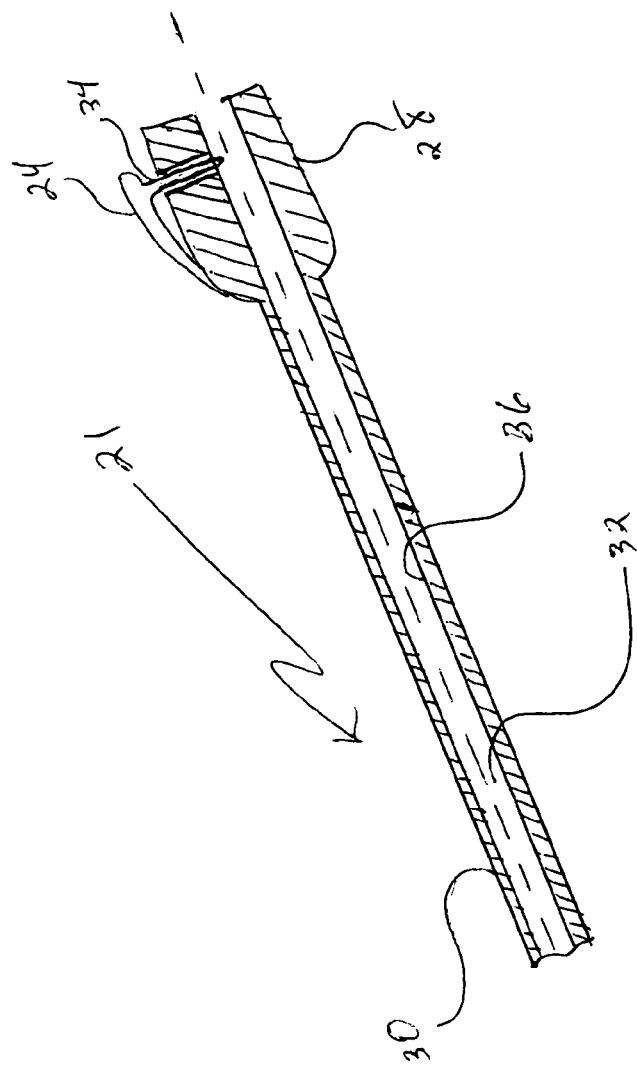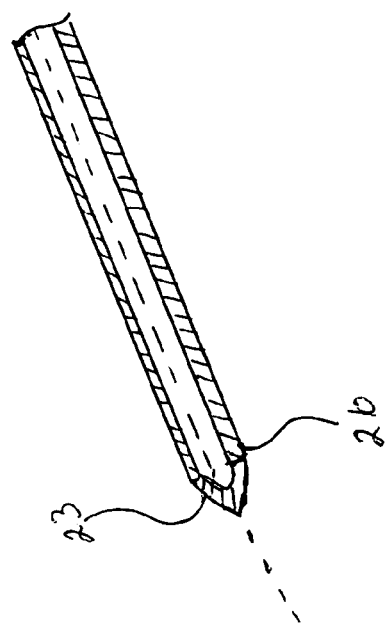

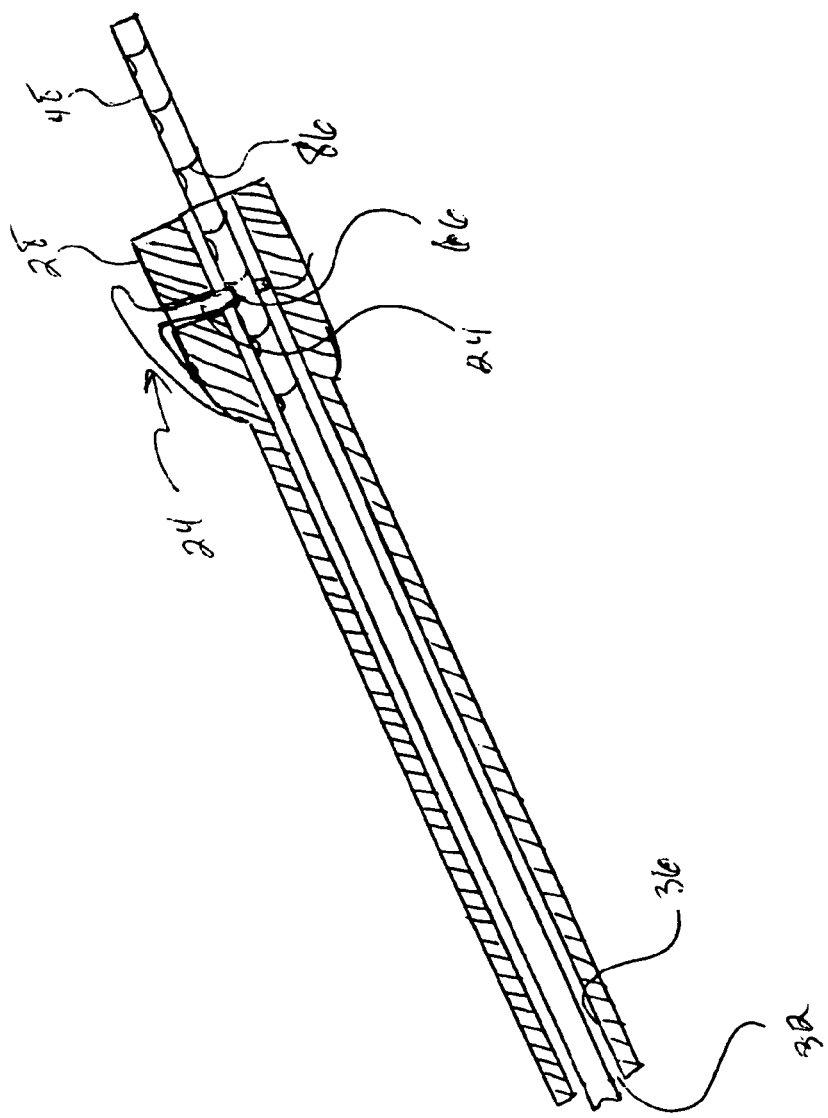
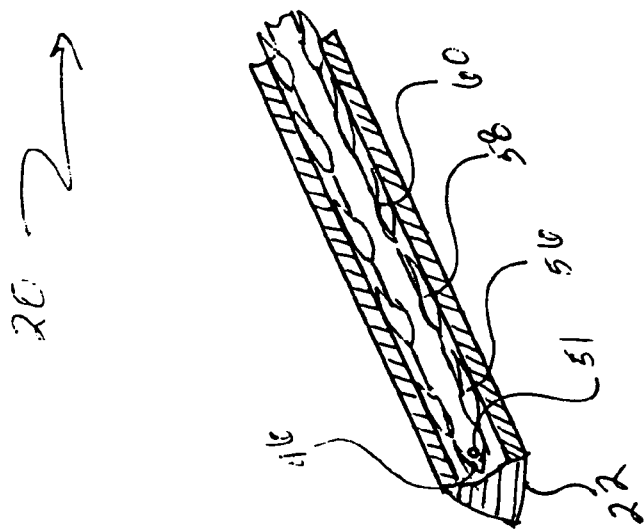
Fig. 7

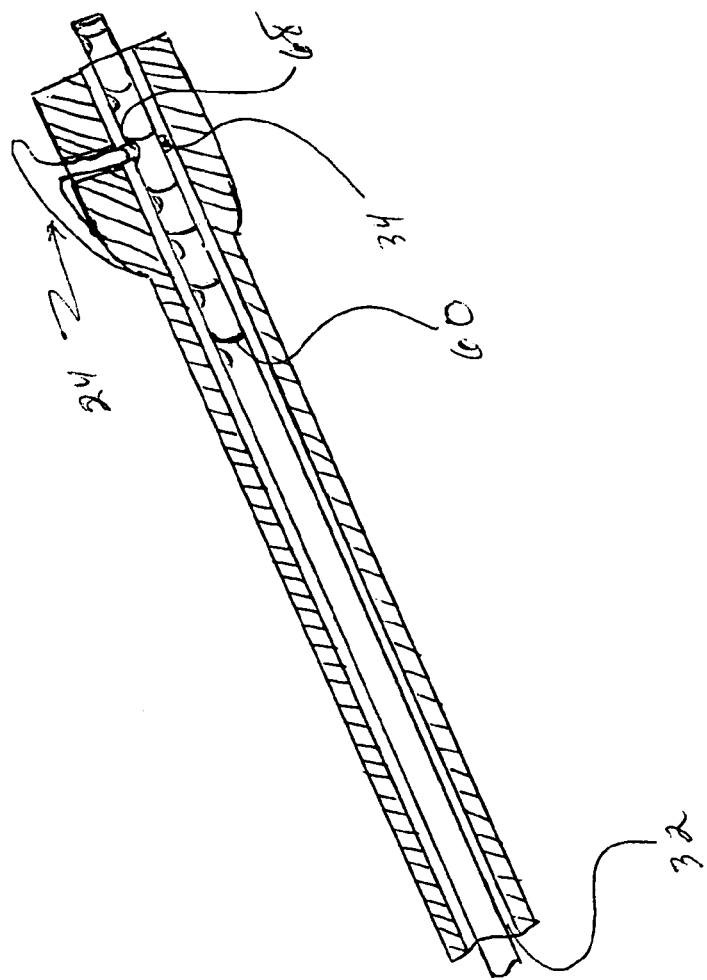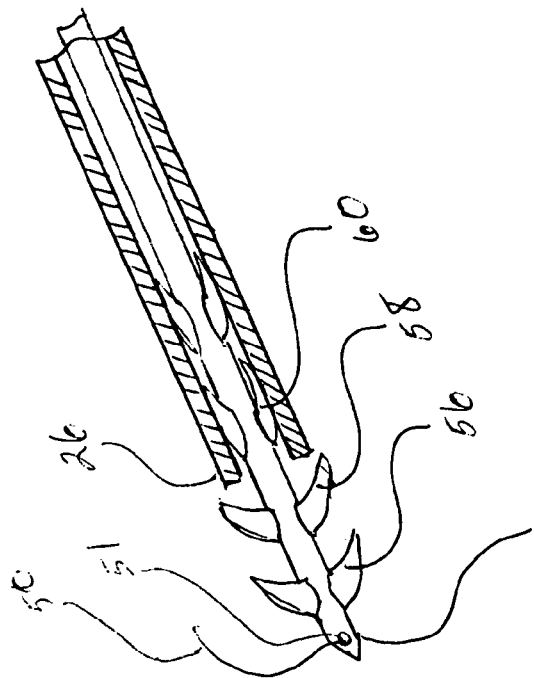
Fig. 8

TISSUE LIFTING DEVICE AND METHOD

BACKGROUND OF THE INVENTION

The present invention relates generally to surgical devices and methods of soft tissue remodeling.

The present invention relates to a new method of soft tissue remodeling to counteract the effects of aging on a person's face and other parts of the body. As a person ages, the skin begins to loosen, sag, and develop wrinkles. In addition to the skin, the supporting structures also relax. Various cosmetic surgical procedures and techniques have been used to remodel the soft tissue, such as a facelift, browlift, necklift, or blepharoplasty. These surgical procedures can incorporate large incisions. Optimally, it would be best to use a few small incisions. It is difficult to uniformly redistribute the tissue using just one or two small incisions without exerting excessive tension on one area of the soft tissue that would produce an unnatural or pulled result.

Consequently, there is a need for further improvement in the relative area including surgical devices and techniques that allow a surgeon to remodel soft tissue to provide a yet produce a pleasing, natural result. The present invention addresses the above-described problems and provides additional benefits and advantages.

SUMMARY OF THE INVENTION

The present invention includes a fixation device, which is placed within the soft tissue, and has prongs on one end and multiple holes on the other end. It also comprises an insertion tool, which allows deployment of this fixation device within the soft tissue for accurate lifting and fixation of the soft tissue to a higher level. There is a locking mechanism on the insertion tool, which allows the fixation device to be held until engagement into the soft tissue is desired. This allows for accurate and adjustable tension on the various depths of the soft tissue. The surgical treatment will consist of making an incision in the patient's soft tissue, inserting the fixation device using the insertion tool, and slowly advancing the fixation member through the insertion tool to engage each successive set of prongs into the soft tissue and applying tension to the fixation device as each prong is being engaged. This successive pull will remodel the soft tissue accurately and allow for adjusting to the individual patient.

In one form, the present invention provides a medical device for treatment of soft tissue. The device comprises an insertion tool that resembles a hypodermic-like tool defining a lumen therethrough. The insertion tool has an insertion end and an opposite, hub end. The device also includes a fixation member that is slidably received within the lumen. The fixation member includes an elongate shaft having a first end and an opposite second end and includes a plurality of prongs fixedly attached to the shaft adjacent the first end and a plurality of holes adjacent the second end.

In preferred embodiments, the insertion tool can also include a locking mechanism or assembly to enable the surgeon to secure the fixation member in the lumen at a first position. The locking mechanism can be released to allow the surgeon to deploy the fixation member to a second position so that the prongs can engage the soft tissue.

In another form, the present invention provides a method of surgical treatment for a patient. The treatment comprises: making an incision in the patient's soft tissue; inserting into the incision a tissue remodeling device including an elongate tissue fixation member having a plurality of tissue engaging prongs disposed within an insertion tool; advancing the tissue fixation member through the insertion tool to engage at least a first one of the plurality of prongs to the soft tissue; and applying tension to the elongate tissue fixation member to effect remodeling of the engaged soft tissue.

In still yet another form, the present invention provides a method of surgical treatment to remodel tissue of a patient. The method comprises making an incision in the tissue of the patient; providing an insertion tool having a lumen and locking assembly and including a fixation member having at least one prong extending outwardly therefrom; and deploying a length of said fixation member into said incision, wherein said fixation member attaches to and lifts the patient's tissue.

BRIEF DESCRIPTION OF THE DRAWINGS

FIG. 3 is a cross-sectional view of one embodiment of an insertion tool with a tissue piercing tip in accordance with the present invention.

FIG. 7 is a cross-sectional view of a tissue remodeling assembly having a fixation member disposed in the insertion tool in accordance with the present invention.

FIG. 8 is a cross-sectional view of the tissue remodeling assembly of FIG. 7 illustrating that a portion of the fixation member can extend beyond the end of the insertion tool in accordance with the present invention.

DETAILED DESCRIPTION OF THE INVENTION

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described devices and/or methods, and any further applications of the principles of the invention as described herein, are contemplated as would normally occur to one skilled in the art to which the invention relates.

Figure 1:
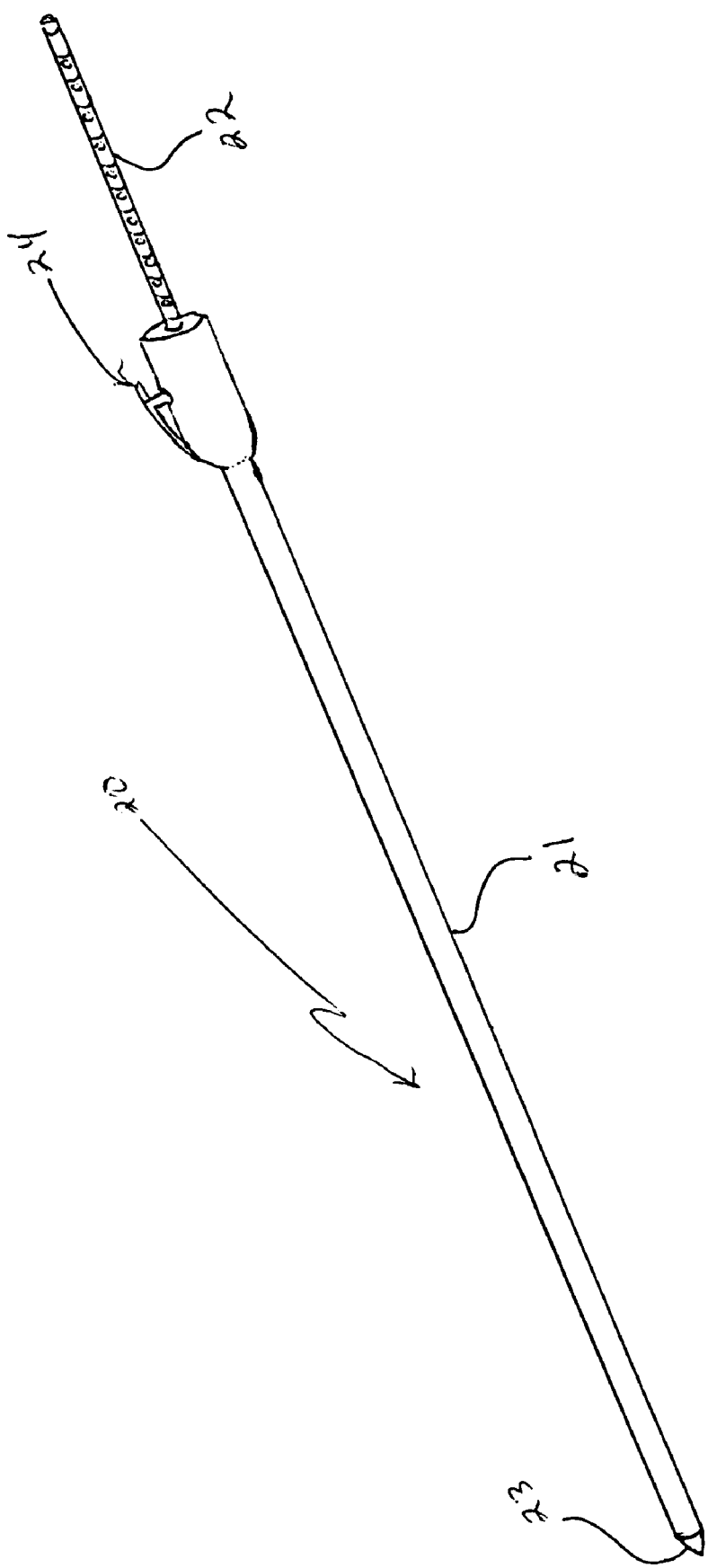
FIG. 1 is a perspective view of one embodiment of the tissue remodeling assembly in accordance with the present invention.

FIG. 1 illustrates one embodiment of a tissue remodeling assembly 20 in accordance with the present invention. Tissue remodeling assembly 20 includes an insertion tool 21 and fixation member 22, which is loaded within the insertion tool. In addition, insertion tool 21 includes a locking assembly 24 to secure and engage the fixation member within.

Figure 2:
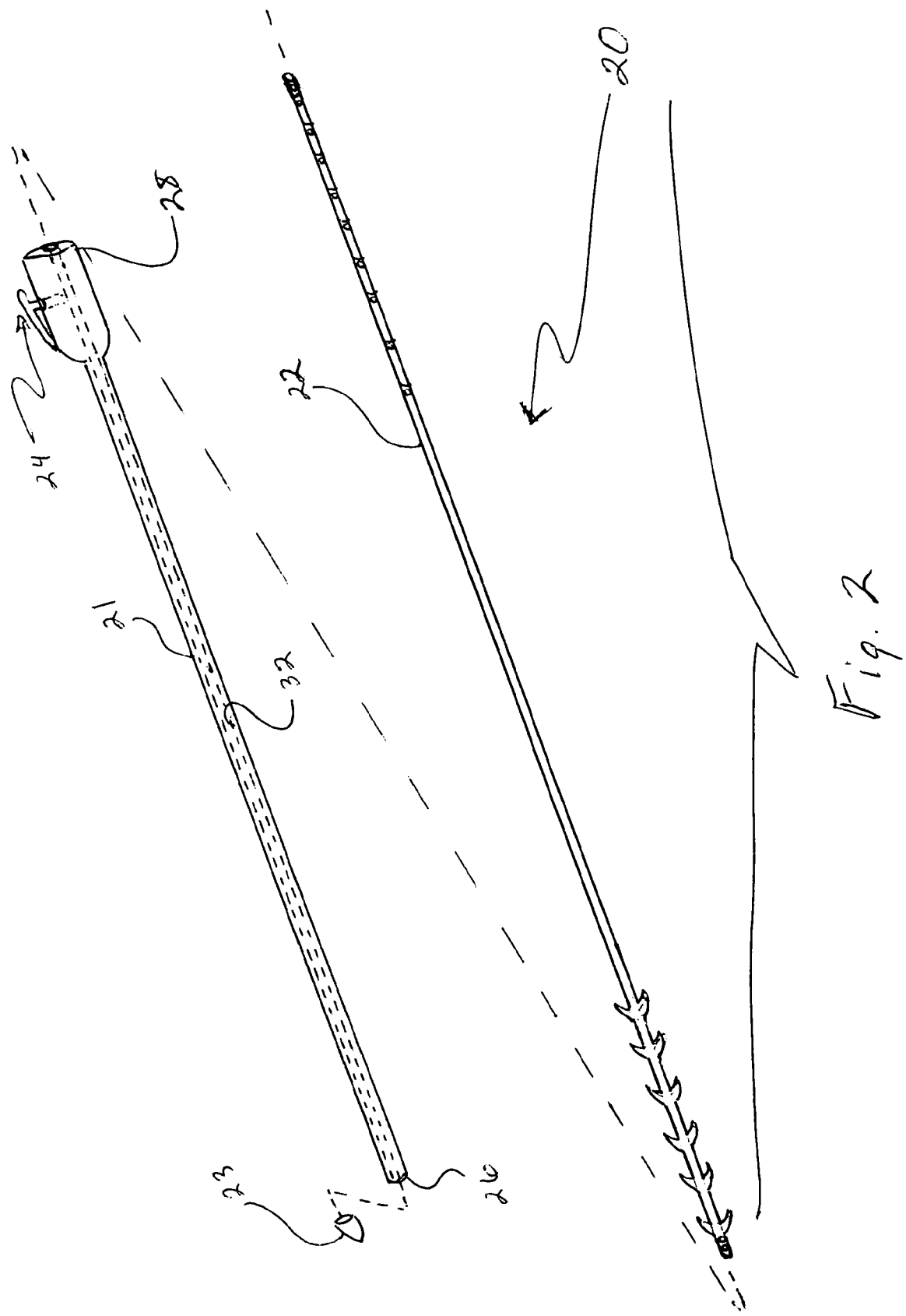
FIG. 2 is an exploded view of the tissue remodeling assembly illustrated in FIG. 1.

Referring now additionally to FIG. 2, in the illustrated embodiment insertion tool 21 is a substantially hollow, hyperdermic-like tool or cannula having a lumen extending through it and with a removable cap 23 at its end. The shaft 30 of the insertion tool terminates on a first end in insertion end 26 and on an opposite end in hub end 28. The outer diameter of insertion tool 21 is sized to permit minimally invasive surgical procedures. The inner diameter or lumen of insertion tool 21 is sized to accept various sizes of fixation members. Examples of specific sizes of fixation devices are preferably between 2 and 5 mm in diameter.

Insertion tool 21 is illustrated as a straight shaft. However, it could be configured to compensate for the natural anatomical features of the human anatomy.

FIG. 3 is a cross sectional view of insertion tool 21 showing its hollow core or lumen 32 and locking assembly 24 to releasably retain the fixation member 22. Locking assembly 24 can be configured to releasably secure the fixation member at a fixed location or depth within the lumen 32 of shaft 30. In the illustrated embodiment, locking assembly 24 includes a pin 34 extending through hub end 28 and into lumen 32. Pin 34 is configured to engage with a corresponding hole or recess on the fixation member (described more fully below). Locking assembly 24 can be biased to retain its position. In one embodiment, locking assembly 24 is biased to force pin 34 to engage with the fixation member received within lumen 32. In an alternative embodiment, locking assembly 24 is biased to force pin 34 to be retracted within the body of hub end 28 and in a non-engaging arrangement with the included fixation member.

In a preferred embodiment, tissue insertion end 26 can include tissue piercing cap 23 removably secured thereon. Tissue piercing cap 23 can be configured with a sharp point to easily pierce tissue with minimal (if any) tearing.

Hub end 28 can be flared and configured to facilitate the gripping and placement of the insertion tool in a desired location. In one embodiment, hub end 28 is provided to have an enlarged exterior diameter to facilitate gripping by the surgeon during use.

Insertion tool 21 can be formed of a variety of rigid biocompatible materials as desired. Preferred materials include stainless steel and surgical steel.

Figure 4:
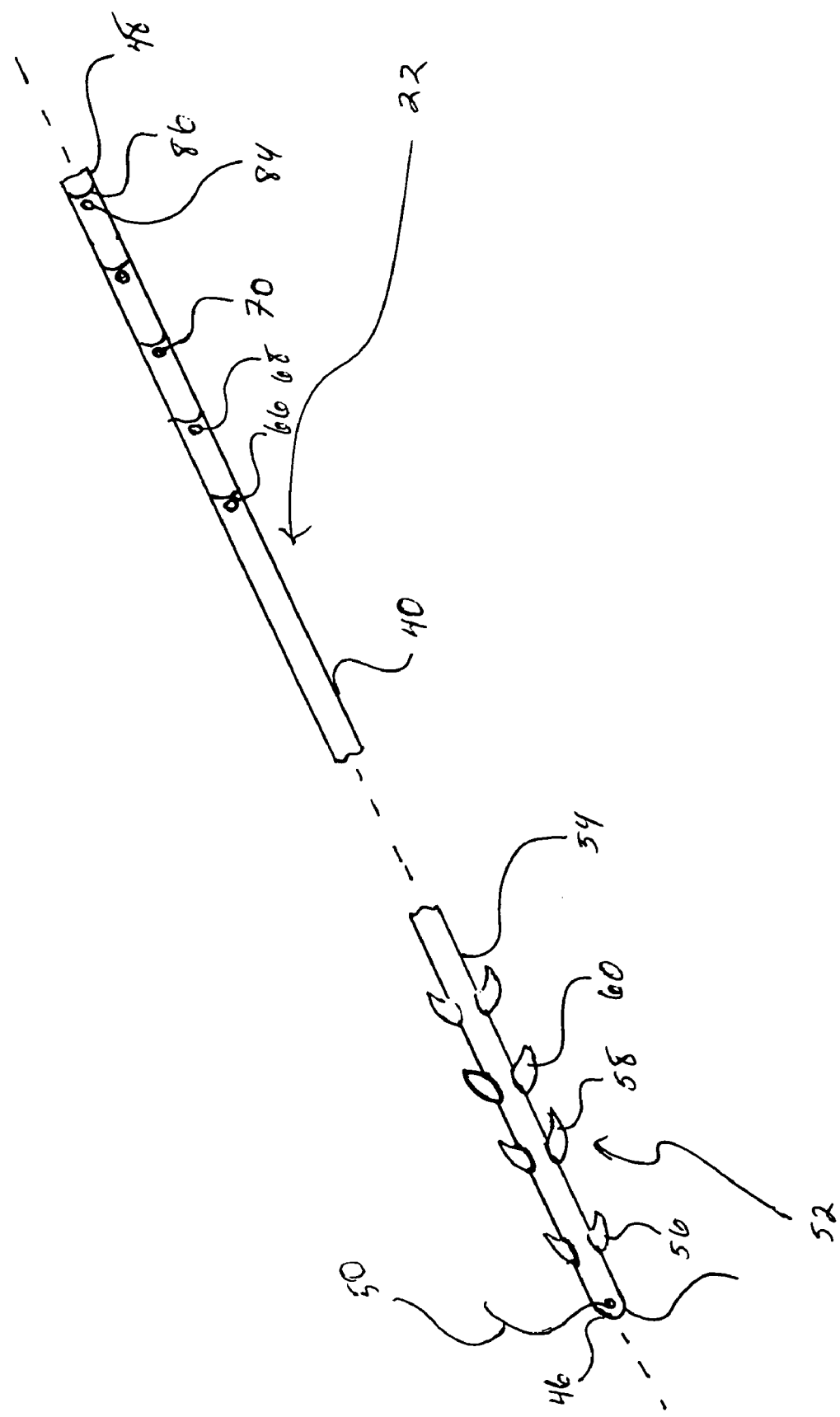
FIG. 4 is a plan view of one embodiment of a tissue fixation member in accordance with the present invention.

FIG. 4 is a plan view of one embodiment of a fixation member 22 for use in the present invention. Fixation member 22 is provided as an elongate shaft 40 that can be provided as a flexible, thin biocompatible cord or rod suitable for implantation into a patient to remodel tissue. In the illustrated embodiment, shaft 40 is configured to exhibit a substantially cylindrical configuration, having a preferred diameter of at least about 2 mm and more preferably at least about 4 mm. For larger areas of tissue lifting, a larger fixation device can be used. It will be understood that shaft 40 can be provided in other configurations including, without limitation, configurations that have a cross section including a rectangle, a square, an oval, or the like in various sizes. The length of fixation member 22 can vary depending upon the area of tissue remodeling.

Shaft 40 includes a first end 46 and an opposite second end 48. First end 46 can include one or more eyes or apertures 50 suitable for receiving a length of suture. The suture can be used to either secure the tip to tissue and/or facilitate retrieval of the fixation member.

A plurality of tissue engaging prongs 52 are also located adjacent first end 46. The prongs extend from the external surface 54 of shaft 40 and are spaced axially from each other. In one embodiment, the prongs are grouped into a plurality of sets of prongs with each set of prongs spaced axially from the other sets. The sets of prongs can include two, three, or more prongs extending symmetrically or asymmetrically about shaft 40. Preferably, the prongs are positioned at 90°, 120°, or 180° from each other. However, it will be understood the prongs can be positioned as needed or desired for the specific tissue to be lifted. Preferably prongs 52 are flexible. Consequently, the prongs 52 may be compressed when inside insertion tool.

Second end 48 of shaft 40 is substantially free of any tissue engaging structures. However, second end 48 includes a plurality of holes. Each of holes 66, 68, and 70 can be provided as an aperture extending completely through shaft 40 or as a recess or indent extending partly through shaft 40. Each hole can be spaced from an adjacent hole that corresponds to the axial spacing between adjacent prongs.

The holes can act as a guide for the surgeon to accurately gauge the length of the flexible device that has been pushed out the distal, first end 46. In addition or in the alternative, the proximal, second end 48 can also include a number of indexing marks or other indicia 86 representative of a unit of length that first end 46 extends beyond insertion end 26 of insertion tool 21. Alternatively, the indexing marks or other indicia 86 can be representative of the number of sets of prongs, that extend beyond the insertion end 26 of insertion tool 21.

Additionally, second end 48 can include a plurality of apertures 84 extending through shaft 40 through which sutures can be threaded to secure fixation member 22 to soft tissue or bone. In one particularly preferred embodiment, the plurality of apertures 84 can also serve or function as holes 68 to engage with pin 34 of locking assembly 24.

Figure 5:
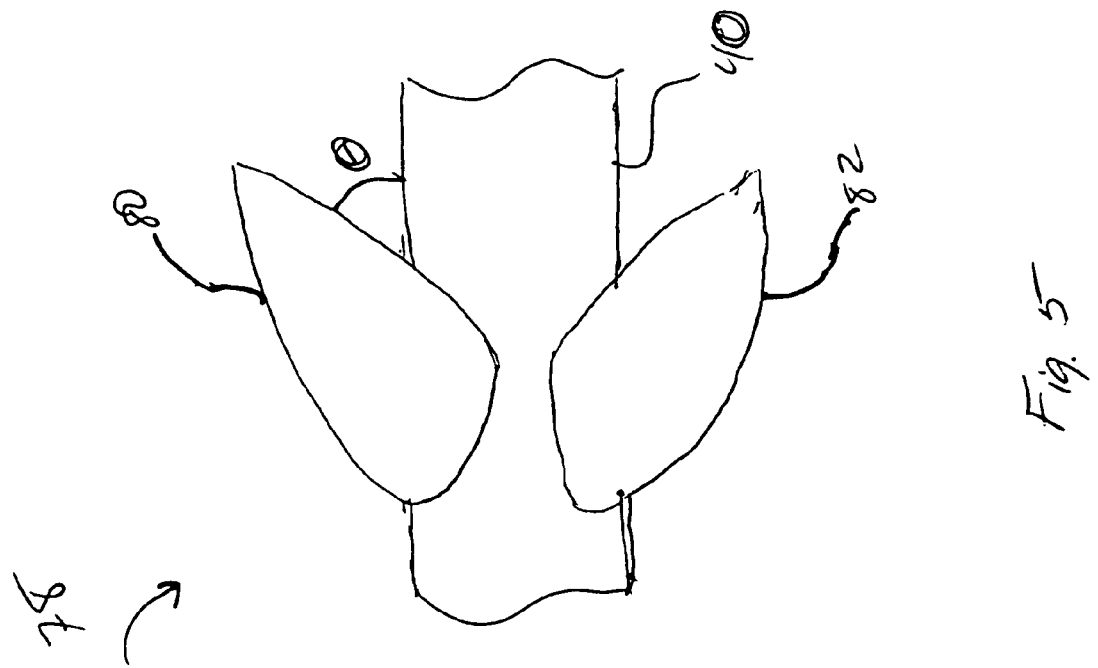
FIG. 5 is an enlarged view of a portion of the fixation member of FIG. 4 illustrating two tissue engaging prongs in accordance with the present invention.

FIG. 5 is an exploded view of one set of prongs 78. In the illustrated embodiment, set of prongs 78 includes two prongs 80 and 82 extending from shaft 40. Each of prongs 80 and 82 are provided to exhibit the profile of a barb or tine to engage and grip surrounding soft tissue. Preferably, prongs 80 and 82 are configured to be easily inserted in tissue in a first direction but difficult to remove from that same tissue when moved or pulled in an opposite, second direction.

Figure 6A:
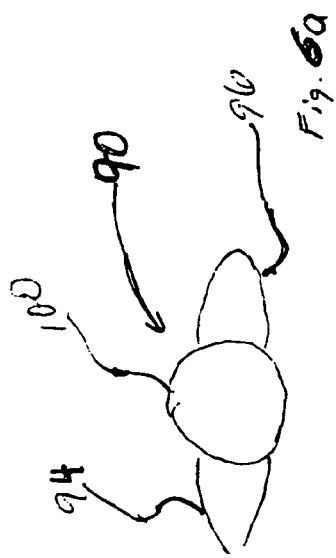
FIGS. 6a and 6b are end views of various fixation members having differing patterns and/or numbers of tissue engaging prongs.
Figure 6B:
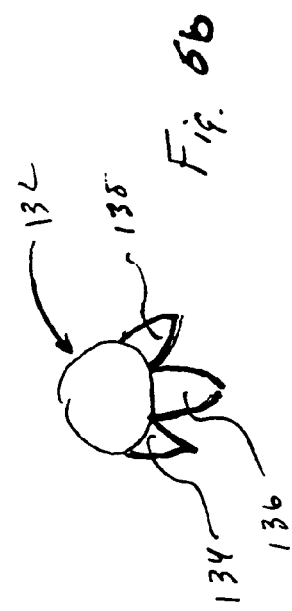

FIGS. 6a and 6b are illustrations a first end view of various shafts for use in the present invention. FIG. 6a illustrates a fixation member 90 having a two prongs 94, and 96 arranged symmetric or diametrically each other about shaft 100. In FIG. 6b, fixation member 132 includes three prongs 134, 136, and 138. As can be seen from the illustrated embodiment, the base of each of prongs 134, 136, and 138 are located on the same hemispherical section of the cylindrical shaped fixation member 132. Consequently, each of prongs 134, 136, and 138 are asymmetrically distributed about the outer circumference of fixation member 132.

Fixation member 22 can be composed of a biocompatible material. The biocompatible material can either be biodegradable or non-biodegradable. Non-limiting examples of non-biodegradable materials for use in the present invention include TEFLON® and polypropylene. In one form, fixation member 22 is provided as a biodegradable material that can slowly degrade in vivo over a period of time ranging between about 6 months and about 24 months.

FIG. 7 is a cross-sectional view of tissue remodeling assembly 20 illustrating fixation member 22 received within lumen 32. In this illustration, it can be observed that the fixation member and the plurality of prongs 52 are sized such that the plurality of prongs 52 are deflected or compressed against the inner wall 36 of lumen 32. Tissue piercing cap 23 is secured to the tissue engaging end of insertion tool 21. On the opposite end of tissue insertion tool 21, locking assembly 24 is provided in a first position whereby pin 34 engages with an hole 66 to axially lock fixation member 22 within lumen 32. It can also be observed that second end 48 of fixation member 22 is exposed beyond hub end 28. Index mark 86 indicates how much of fixation member is exposed.

FIG. 8 is an illustration of tissue remodeling assembly 20 in which tissue piercing cap 23 has been removed. Fixation member 22 has been extended such that first end 46 extends beyond insertion end 26, exposing at least a first set of prongs 56. Additionally, it can be observed that a thread or suture 50 has been inserted through the opening 51 in first end 46 of fixation member 22.

In the illustration, locking assembly 24 has been adjusted to position pin 34 to end through a second hole 68, thereby locking fixation member 22 as desired in the interior lumen 32 of insertion tool 21. In this embodiment, insertion tool 21 can be manipulated to either further insert the insertion tool into tissue or to begin pulling and extracting the insertion tool out of the adjacent soft tissue to begin to effect tissue remodeling.

Figure 9:
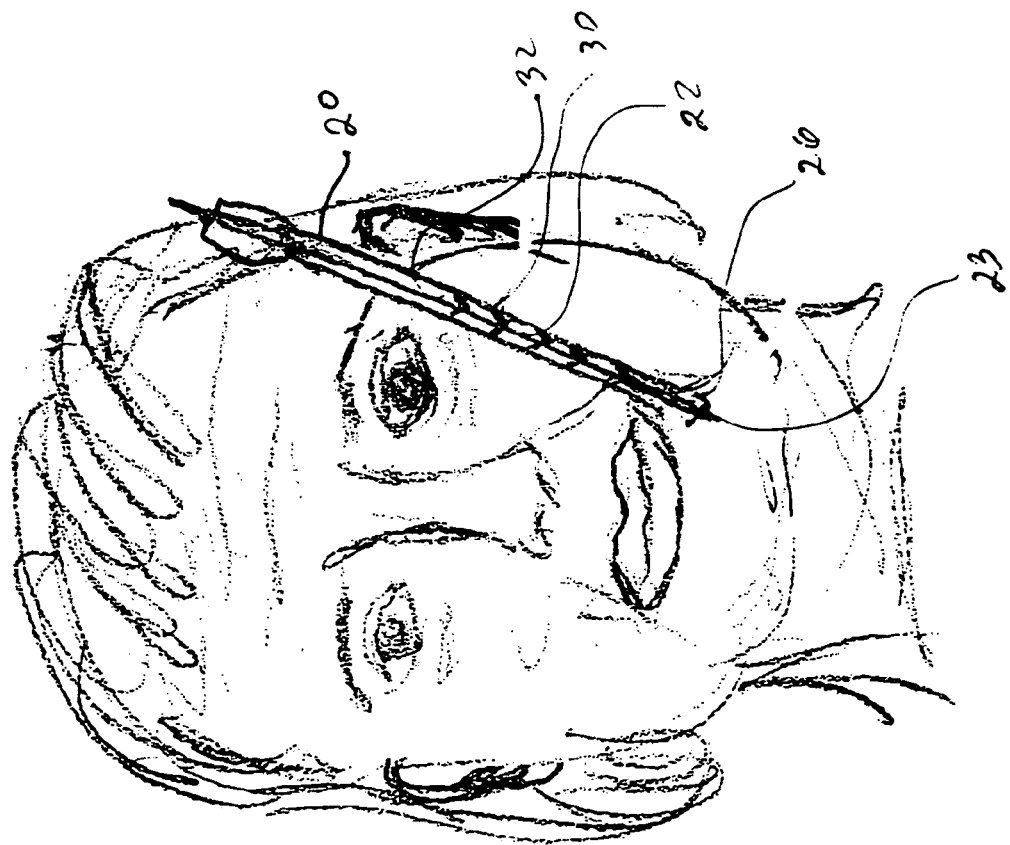
FIG. 9 is an illustration of the tissue remodeling assembly in use in accordance with the present invention.

FIG. 9 is a schematic illustration of the tissue remodeling assembly 20 in use to accomplish tissue remodeling such as that prescribed for a face lift. However, it should be understood that tissue remodeling assembly 20 of the present invention could be used in any general surgical procedure to manipulate soft tissue in other areas of the body.

Figure 10:
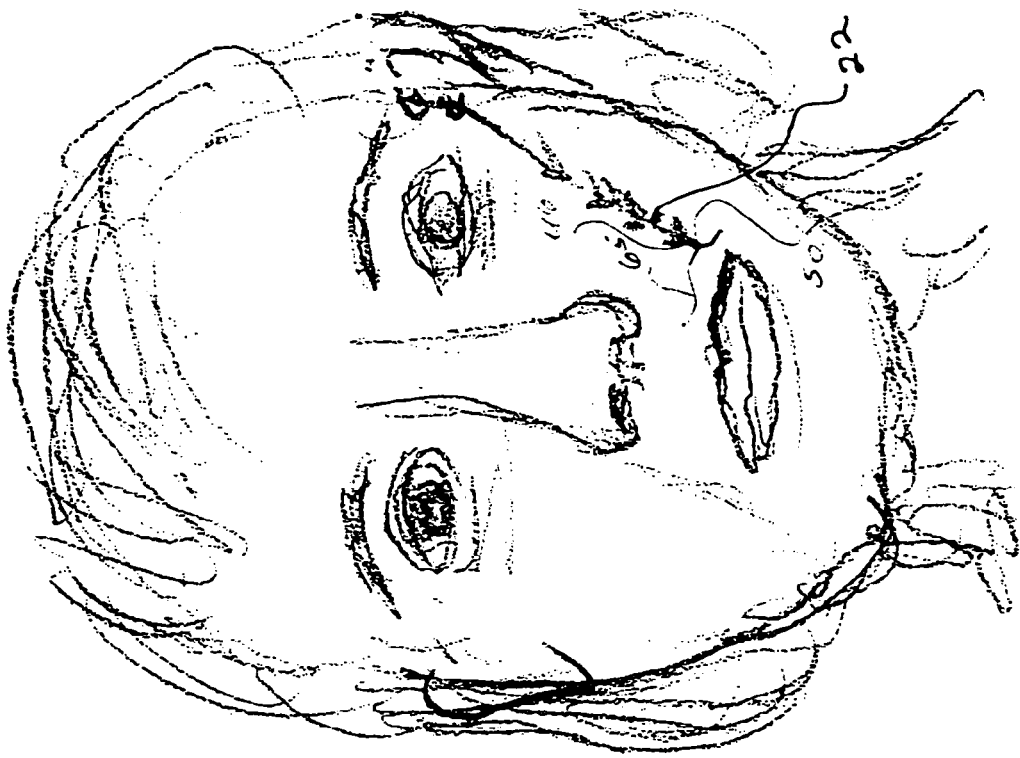
FIG. 10 is an illustration of the fixation member holding the remodeled tissue in place in accordance with the present invention.

A small incision will be made in the temple area of the face and the insertion tool with the loaded fixation device will be placed through this incision and brought down into the buccal or cheek sulcus of the mouth. Because of the removable cap on the insertion end of the tool, non-traumatic passage of this tool can be accomplished. The removable cap is then removed within the mouth and a suture placed through the single hole on the distal end of the fixation device. This is used to stabilize the fixation device initially and to allow removal of the fixation device if it is found not to be in the correct position. The surgeon will then begin the engagement of the fixation device within the soft tissue. This will be accomplished by pushing the fixation device out of the insertion tool slowly. As each prong is released from within the insertion tool, it will then spring open and engage the soft tissue. By placing tension on the insertion tool, elevation of this specific soft tissue can be done. When the proper lift is produced in this part of the soft tissue, another prong can be released and engaged and again, tension and lift can be placed on the second prong, which will then lift this second area of soft tissue. By alternately releasing a prong and lift, an accurate remodeling of the soft tissue can be done. When all the prongs are released, the excess portion of the fixation device can be cut and discarded, leaving the remaining portion with holes to be fixed to the soft tissue in the temple area. The incision in the temple area then can be easily closed (FIG. 10). A second fixation device can be placed in adjacent tissue if desired through the same or a separate incision. Because each of the fixation device prongs can be deployed individually and tension adjusted for each set of prongs, accurate remodeling of the soft tissue can be accomplished.

The present invention contemplates modifications to the tissue remodeling assembly and its components as would occur to those skilled in the art. It is also contemplated that processes embodied in the present invention can be altered, rearranged, or added to other surgical procedures or medical treatments as would occur to those skilled in the art without departing from the spirit of the present invention.

Unless specifically identified to the contrary, all terms used herein are used to include their normal and customary terminology. Further, while various embodiments of the tissue remodeling assembly, insertion tool, and fixation member having specific components, prongs, dimensions, and structures are described and illustrated herein, it is to be understood that any selected embodiment can include one or more of the specific components and/or structures described for another embodiment where possible.

Further, any theory of operation, proof, or finding stated herein is meant to further enhance understanding of the present invention and is not intended to make the scope of the present invention dependent upon such theory, proof, or finding.

While the invention has been illustrated and described in detail in the drawings and foregoing description, the same is considered to be illustrative and not restrictive in character, it is understood that only the preferred embodiments have been shown and described and that all changes and modifications that come within the spirit of the invention are desired to be protected.

What is claimed is:

1. A medical device for treatment of soft tissue, said device comprising:
 an insertion tool comprising an elongate cannula defining a lumen therethrough and having a first insertion end and a second end opposite thereto, and a locking assembly secured to said elongate cannula proximate to said second end; and
 a fixation member slidably received within the lumen, said fixation member comprising an elongate shaft having a distal end and an opposite proximal end, said elongate shaft including a plurality of prongs fixedly attached to the elongate shaft adjacent the distal end and a plurality of holes or recesses adjacent the proximal end, wherein said locking assembly is constructed and arranged to selectively engage said plurality of holes or recesses to lock said fixation member at a desired position with respect to said insertion tool and to selectively disengage from said plurality of holes or recesses to permit relative movement of said fixation member with respect to said insertion tool.

2. The device of claim 1 comprising a tissue piercing tip removably secured to the first insertion end of the insertion tool.

3. The device of claim 1 wherein the locking assembly comprises a biased lever and pin, said pin constructed and arranged to extend into the lumen and repeatedly engage and disengage the holes or recesses in the fixation member.

4. The device of claim 1 wherein the plurality of prongs extend laterally away from the elongate shaft.

5. The device of claim 1 wherein the fixation member further comprises a plurality of sets of prongs each set of prongs spaced axially along the elongate shaft from an adjacent set of prongs.

6. The device of claim 5 wherein the plurality of sets of prongs comprises two prongs extending from the elongate shaft diametrically opposite each other.

7. The device of claim 5 wherein the prongs are positioned asymmetrically about the elongate shaft.

8. The device of claim 1 wherein each prong of the plurality of prongs is flexible.

9. The device of claim 1 wherein the lumen of the elongate cannula has a radius selected to deform each prong of the plurality of prongs positioned therein.

10. The device of claim 1 wherein the lumen of the elongate cannula has a radius selected to be between about 2 mm and about 5 mm.

11. The device of claim 1 wherein the holes or recesses are axially spaced from each other by a distance representative of the length that the distal end extends beyond the insertion end of the elongate cannula.

12. The device of claim 1 wherein the fixation member further comprises a plurality of indexing marks representative of either a length that the distal end extends beyond the insertion end of the elongate cannula or the number of prongs that are exposed beyond the insertion end of the elongate cannula.

13. The device of claim 1 wherein the fixation member is non biodegradable.

14. The device of claim 1, wherein the fixation member further comprises an eye or aperture on the distal end suitable for receiving a length of suture.

15. The device of claim 1, wherein the locking assembly is constructed and arranged to repeatedly selectively engage and disengage the plurality of holes or recesses to lock and unlock said fixation member with respect to said insertion tool at multiple positions.

16. A method of surgical treatment comprising;
making an incision in soft tissue adjacent to a tissue portion to be remodeled;
inserting a portion of the device of claim 1 through the incision to secure to the tissue portion to be remodeled; and
applying tension to the device of claim 1 to manipulate the tissue portion to be remodeled.

17. The method of claim 16, further comprising the step of suturing the distal end of the fixation member in place through an eye or aperture in the fixation member.

18. A medical device for treatment of soft tissue, said device comprising:
an insertion tool comprising an elongate cannula, a first insertion end and a second opposite end, wherein said elongated cannula defines a lumen therethrough; and
a fixation member slidably received within the lumen, said fixation member comprising an elongate shaft having a distal end and a proximal end, said elongate shaft comprising a plurality of prongs adjacent the first end, a plurality of holes or recesses adjacent the proximal end, and a plurality of indexing marks adjacent the proximal end, said indexing marks representative of an amount that the fixation member extends beyond the insertion end or a number of prongs exposed beyond the insertion end of the insertion tool;
wherein the insertion tool further comprises a biased locking assembly secured to said elongate cannula proximate to the second opposite end, said locking assembly being constructed and selectively engage said plurality of holes or recesses to lock said fixation member at a desired position with respect to said insertion tool and to selectively unlock said fixation member thereby permitting relative movement of said fixation member with respect to said insertion tool inside the lumen of said insertion tool.

19. The device of claim 18 comprising a tissue piercing tip removably secured to the first insertion end of the insertion tool.

20. The device of claim 18 wherein the biased locking assembly comprises a biased lever and pin, said pin constructed and arranged to extend into the lumen and repeatedly engage and disengage the fixation member.

21. The device of claim 18 wherein the fixation member comprises a plurality of sets of prongs, each set of prongs spaced axially along the elongate shaft.

22. The device of claim 18 wherein each of the plurality of prongs is flexible.

23. The device of claim 18 wherein the lumen of the cannula has a radius selected to deform the prongs positioned therein.

24. The device of claim 18, wherein the fixation member further comprises an eye or aperture on the distal end suitable for receiving a length of suture.

25. A method of surgical treatment for a patient, said treatment comprising making an incision in soft tissue adjacent to a tissue portion to be remodeled;
inserting a portion of the device of claim 18 through the incision to secure to the tissue portion to be remodeled; and
applying tension to the device of claim 18 to manipulate the tissue portion to be remodeled.

26. The method of claim 25, further comprising the step of suturing the distal end of the fixation member in place through an eye or aperture in the fixation member.

27. A method of surgical treatment for a patient, said treatment comprising:
making an incision in the patient's soft tissue;
inserting into the incision a tissue remodeling device including an elongate tissue fixation member having a plurality of tissue engaging prongs and a plurality of holes or recesses disposed within an insertion tool that includes a locking assembly secured proximate to a proximal end of the insertion tool wherein the locking assembly is constructed and arranged to repeatedly selectively engage and disengage the plurality of holes or recesses to selectively lock and unlock the fixation member at desired positions with respect to the insertion tool;
advancing the tissue fixation member relative to the insertion tool to engage at least a first one of the plurality of prongs to the soft tissue;
using the locking assembly, releasably locking the elongate tissue fixation member in the insertion tool at a first position wherein at least a first one of the plurality of prongs engages the patient's soft tissue;
applying tension to the elongate tissue fixation member to effect remodeling of the engaged soft tissue; and
using the locking assembly, unlocking the elongate tissue fixation member from the insertion tool and advancing the fixation member relative to the insertion tool to a second position wherein at least a second one of the tissue engaging prongs engages the patient's soft tissue.

28. The method of claim 27, further comprising the step of, prior to the applying tension step, suturing the tissue fixation member in place through an eye or aperture in the tissue fixation member.

29. A method of surgical treatment for a patient, said treatment comprising:
making an incision in the patient's soft tissue;
inserting into the incision a tissue remodeling device including an elongate tissue fixation member having a plurality of tissue engaging prongs disposed within an insertion tool;
advancing the tissue fixation member relative to the insertion tool to engage at least a first one of the plurality of prongs to the soft tissue;
releasably locking the elongate tissue fixation member in the insertion tool at a first position wherein at least a first one of the plurality of prongs engages the patient's soft tissue;
applying tension to the elongate tissue fixation member to effect remodeling of the soft tissue engaged by the first one of the plurality of prongs; and subsequently to effecting remodeling of the soft tissue engaged by the first one of the plurality of prongs, unlocking the elongated tissue fixation member from the insertion tool at the first position, pushing the elongated tissue fixation member further out of the insertion tool to engage at least a second one of the plurality of prongs to the soft tissue, releasable locking the elongated tissue fixation member in the insertion tool and applying tension to the elongated tissue fixation member to effect remodeling of the soft tissue engaged by at least the second one of the plurality of prongs;

wherein the elongate tissue fixation member comprises a cylindrical shaft having a plurality of sets of prongs, each set of prongs axially spaced from an adjacent set of prongs.

30. The method of claim 29 wherein each plurality of sets of prongs includes two or more individual prongs.

31. The method of claim 30 comprising applying tension to the elongate tissue fixation member to effect uniform remodeling of the tissue in a direction collinear with a length of the elongate tissue fixation member.

32. The method of claim 29, further comprising the step of, prior to the applying tension step, suturing the tissue fixation member in place through an eye or aperture in the tissue fixation member.

33. A method of surgical treatment for a patient, said treatment comprising:

making an incision in the patient's soft tissue;

inserting into the incision a tissue remodeling device including an elongate tissue fixation member having a plurality of tissue engaging prongs and a plurality of holes or recesses disposed within an insertion tool that includes a locking assembly secured proximate to a proximal end of the insertion tool wherein the locking assembly is constructed and arranged to repeatedly selectively engage and disengage the plurality of holes or recesses to selectively lock and unlock the fixation member at desired positions with respect to the insertion tool;

for at least a first one of the plurality of prongs, partially extracting the insertion tool from the incision to engage the at least first one of the plurality of prongs to the soft tissue, using the locking assembly, releasably locking the elongate tissue fixation member in the insertion tool at a first position, and applying tension to the insertion tool at the first position to effect remodeling of the engaged soft tissue by the at least first one of the plurality of prongs; and subsequently for at least a second one of the plurality of prongs, using the locking assembly, unlocking the elongate tissue fixation member from the insertion tool at the first position, further partially extracting the insertion tool from the incision to engage the at least second one of the plurality of prongs to the soft tissue, using the locking assembly, releasably locking the elongate tissue fixation member in the insertion tool at a second position, and applying tension to the insertion tool at the second position to effect remodeling of the engaged soft tissue by the at least second one of the plurality of prongs.

34. The method of claim 33, further comprising the step of, after the inserting step, suturing the tissue fixation member in place through an eye or aperture in the fixation member.

\* \* \* \* \*

UNITED STATES PATENT AND TRADEMARK OFFICE
CERTIFICATE OF CORRECTION

| | | |
|---|---|---|
| PATENT NO. | : 7,850,700 B2 | Page 1 of 1 |
| APPLICATION NO. | : 10/848698 | |
| DATED | : December 14, 2010 | |
| INVENTOR(S) | : Chester Y. Sakura, Jr. | |

It is certified that error appears in the above-identified patent and that said Letters Patent is hereby corrected as shown below:

Column 7, line 60 (Claim 23, line 1) insert the word --elongate-- after the word "the" and before the word "cannula"

Column 8, line 56 (Claim 29, line 14) insert the word --and-- after the word "tissue"

Signed and Sealed this
Twelfth Day of April, 2011

David J. Kappos
*Director of the United States Patent and Trademark Office*